(12) United States Patent
Wang et al.

(10) Patent No.: US 11,553,891 B2
(45) Date of Patent: Jan. 17, 2023

(54) AUTOMATIC RADIOGRAPHY EXPOSURE CONTROL USING RAPID PROBE EXPOSURE AND LEARNED SCENE ANALYSIS

(71) Applicant: CARESTREAM HEALTH, INC., Rochester, NY (US)

(72) Inventors: Xiaohui Wang, Pittsford, NY (US); Martin S. Pesce, Quakertown, PA (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 16/868,609

(22) Filed: May 7, 2020

(65) Prior Publication Data

US 2020/0359986 A1 Nov. 19, 2020

Related U.S. Application Data

(60) Provisional application No. 62/846,783, filed on May 13, 2019.

(51) Int. Cl.
*A61B 6/00* (2006.01)

(52) U.S. Cl.
CPC .............. *A61B 6/542* (2013.01); *A61B 6/461* (2013.01); *A61B 6/467* (2013.01)

(58) Field of Classification Search
CPC ......... A61B 6/542; A61B 6/461; A61B 6/467; A61B 6/405; A61B 6/52–5; A61B 6/032; A61B 6/025; A61B 6/0414; A61B 6/482; A61B 6/502

See application file for complete search history.

(56) References Cited

U.S. PATENT DOCUMENTS

2016/0242712 A1* 8/2016 Jin .......................... A61B 6/488
2018/0049714 A1* 2/2018 Nett ..................... A61B 6/0487
2018/0333129 A1* 11/2018 Toepfer ................ A61B 6/5223

* cited by examiner

*Primary Examiner* — Don K Wong (57) ABSTRACT

A digital radiographic image of a subject is captured using a reduced exposure level of an x-ray source. One or more exposure control regions in the image is mapped and associated with a predetermined exposure level. A difference between the predetermined exposure level setting and the reduced exposure level is used to set a diagnostic exposure level perhaps about twice as high as the reduced exposure level to capture a diagnostic image of the subject.

19 Claims, 7 Drawing Sheets

AUTOMATIC RADIOGRAPHY EXPOSURE CONTROL USING RAPID PROBE EXPOSURE AND LEARNED SCENE ANALYSIS

CROSS REFERENCE TO RELATED APPLICATIONS

This application claims priority to U.S. Patent Application Ser. No. 62/846,783, filed May 13, 2019, in the name of Wang, et al., and entitled AUTOMATIC RADIOGRAPHY EXPOSURE CONTROL USING RAPID PROBE EXPOSURE AND LEARNED SCENE ANALYSIS, which is hereby incorporated by reference herein in its entirety.

BACKGROUND OF THE INVENTION

The disclosure relates generally to the field of radiographic imaging, and in particular to exposure control. More specifically, the disclosure relates to apparatus and methods for automatically designating suitable areas of a digital radiography (DR) detector for exposure measurement.

Automatic Exposure Control (AEC) apparatus have been widely used in conventional diagnostic X-ray equipment to control X-ray exposure levels received by a patient. An AEC device, positioned at a suitable location in the exposure path, tracks how much radiation has been received for an image. At a predetermined threshold value, the AEC apparatus generates an output signal which is then used to disable power to the X-ray emission components, thereby terminating the generation of ionizing radiation for that image.

With the advent of Digital Radiography (DR) imaging, approaches have been proposed for integrating AEC functions within the DR imaging panel, such as employing portions of the pixel array for exposure control. This would appear to have appreciable benefits if it could be achieved. However, practical limitations including spacing and panel size, component complexity, and cost as well as the need to adapt the AEC configuration suitably for patients of different size and condition, greatly complicate this task.

It can be appreciated that there would be benefits to providing a measure of exposure control using the DR imaging panel without requiring modification to DR panel components and without perceptible delay in the imaging workflow, particularly where such a solution can provide a measure of adaptability with reduced risk of operator error.

The discussion above is merely provided for general background information and is not intended to be used as an aid in determining the scope of the claimed subject matter.

BRIEF DESCRIPTION OF THE INVENTION

A digital radiographic image of a subject is captured using a reduced exposure level of an x-ray source. One or more exposure control regions in the image is mapped and associated with a predetermined exposure level. A difference between the predetermined exposure level setting and the reduced exposure level is used to set a diagnostic exposure level perhaps about twice as high as the reduced exposure level to capture a diagnostic image of the subject.

In one embodiment, a computer implemented method includes capturing a reduced exposure DR image of a subject in a DR detector. One or more exposure control regions are mapped in the reduced exposure DR image and a predetermined exposure level is associated therewith. A difference between the predetermined exposure level setting and the reduced exposure level is calculated and used to set the x-ray source for a diagnostic image capture of the subject.

In one embodiment, a computer implemented method includes capturing a reduced exposure DR image of a subject in a DR detector in response to an operator command entry. One or more exposure control regions are mapped in the reduced exposure DR image and a predetermined exposure level is associated therewith using an output from a machine learning algorithm. A difference between the predetermined exposure level setting and the reduced exposure level is calculated and used to automatically set the x-ray source for a diagnostic image capture of the subject.

In one embodiment, a digital radiography system has an x-ray generator, a digital radiography detector panel, a display in for displaying acquired DR images, and a control logic processor communicating therewith. The control logic processor is configured to energize the x-ray generator, in response to an operator instruction, at a reduced exposure setting toward a subject and the digital radiography detector panel. The processor acquires a reduced-exposure image of the subject from the digital radiography detector panel and momentarily suspends the x-ray generator while executing a sequence to: map, within the reduced-exposure image of the subject, one or more exposure control measurement regions, associate a predetermined target clinical exposure setting with the one or more mapped exposure control measurement regions, calculate a difference between the reduced exposure setting and the associated predetermined target clinical exposure setting, scale a clinical exposure setting according to the calculated difference; resume x-ray beam generation by the x-ray generator at the scaled clinical exposure setting, and acquire a diagnostic digital radiographic image of the subject from the digital radiography detector panel.

An object of the present disclosure is to advance the art of digital radiographic imaging with respect to exposure measurement and control. A further object of the disclosure is to address difficulties and shortcomings of existing methods for exposure control, as noted in the Background section.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE EMBODIMENTS

The following is a detailed description of the preferred embodiments, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the image processing context of the present disclosure, "rendering" is the active process of generating and forming a digital image for display and generating the pattern of electronic signals needed for displaying it to a user. A digital image file may contain data objects in a strictly defined language or data structure, defining aspects of the image content such as geometry, viewpoint, texture, lighting, and shading information as a description of a scene. The data contained in the scene content or scene file is passed to a rendering program to be processed and output or streamed to a display driver or graphics processing unit (GPU) for direct presentation on a display or to a digital image or raster graphics image file. The digital image data file can alternately be available for presentation on a display. The same image content can be rendered, for example, on a monochrome display or in color on a full color display.

With respect to an image detector, the term "pixel" refers to a picture element unit cell containing a photo-conversion circuit and related circuitry for converting incident electromagnetic radiation to an electrical signal. The term "subject" or "subject anatomy" refers to the optical object that is imaged by the x-ray imaging apparatus.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

The term "highlighting" for a displayed feature has its conventional meaning as is understood to those skilled in the information and image display arts. In general, highlighting uses some form of localized display enhancement to attract the attention of the viewer. Highlighting a portion of an image, such as a marker or an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

In typical applications, a computer or other type of dedicated logic processor for obtaining, processing, and storing image data is part of the radiography system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random-access memory (RAM) that is used for shorter term storage, such as employed to store a computer program having instructions for controlling one or more computers to practice the method according to the present invention.

Default AEC positions are impractical, primarily due to differences in patient size. Manual AEC placement designation for DR applications takes considerable time and requires a significant amount of experience for achieving acceptable results. Automated methods, however, have exhibited other problems. The Applicant has found that conventional methods for image analysis, segmentation, and other processes generally used for re-mapping AEC placement can be time-consuming, resource-intensive, and often provide erroneous or disappointing results. Disparities in anatomical position can cause poor AEC placement. In addition, even for two patients with the same AEC positioning, tissue density or thickness differences between patients can also affect the actual exposure value received.

In light of the shortcomings of previous approaches, embodiments of the present disclosure address the difficulties that prevent AEC sensing using the DR detector by using high speed logic processing to quickly characterize image features from a low-exposure probe image. A machine-learning algorithm is trained to recognize anatomy features in the low-exposure probe image and to identify or map appropriate regions for measurement of exposure with reference to the low-exposure probe image. The low-exposure probe image has higher noise content and would not be considered acceptable for diagnostic purposes; the noise content exceeds that of an image that has acceptable exposure for clinical use. Although it operates on images of high noise content, the machine-learning logic is trained on archived images of at least clinical/diagnostic quality, with perceptibly lower noise content, and further provides an association of clinical exposure settings that are suitable for the imaged anatomy. Thus, the machine-learning logic must transform information obtained from high-quality images to images of less than diagnostically acceptable quality in order to identify or map a suitable set of pixels for exposure calculation.

With the goal of improved accuracy and efficiency, the methods described herein briefly suspend exposure during image analysis and re-initiate exposure immediately following pixel re-mapping or, alternately, instruct the operator to confirm or to reconfigure the re-mapping before exposure can be re-initiated.

By analyzing reduced-exposure image content, and quickly identifying area(s) of the image that are most useful for determining a suitable exposure level, methods of the present disclosure effectively substitute calculated values from exposed pixels of the DR imaging panel for AEC sensing. The method of the present disclosure supplants the real-time AEC function by applying logic that is trained to recognize the imaged anatomy in a high noise, reduced-exposure image that is captured in an instant before the full exposure image of clinical quality is obtained. For example, the process of mapping of pixels used for exposure measurement, calculation of appropriate exposure based on coarse exposure information from the reduced-exposure image, and setting of values for clinical image exposure can all take place within 250 msec or less.

In some types of radiography applications, particularly for 3D volume imaging systems, one or more initial sampling exposures are sometimes obtained and assessed in order to help determine what technique settings are most appropriate for image acquisition in subsequent imaging of a particular patient. This can include settings such as kVp potential and mAs technique settings, for example. In such applications, at least one low-dosage initial exposure, sometimes termed a "probe image" or "scout image", is first obtained, then examined by an operator or processed as a guideline to optimizing technique settings. Once the proper technique settings are obtained, image acquisition can begin, such as acquisition of a sequence of 2D projection images.

By contrast, embodiments of the present disclosure are directed to the problem of accumulated exposure that is traditionally handled by the AEC. Rather than for determining suitable technique settings for initiating exposure in the first place, embodiments of the present disclosure make use of an initial sampling exposure to determine the overall amount of exposure that is to be received, based on the response of specific patient anatomy to low level exposure energy. The probe exposure of an embodiment is first used to characterize the type of x-ray image according to its pattern, then to map one or more regions of the image that provide the most useful information relating to the needed exposure levels. Results from these mapped regions can then be used to calculate how much exposure energy is to be received and to effectively provide the AEC function based on the calculation, without the need for deploying an AEC device itself.

Radiation dose, typically expressed in units of millisievert (mSv), is a function of a number of factors, but are largely dependent on two parameters: tube current and exposure time. Exposure, and consequently radiation dose, is typically expressed in units of mAs, as a product of tube current and time. Increasing the mAs (by increasing tube current or extending the exposure time) increases the dose proportionally: a level of 300 mAs for the same time period delivers nominally about twice the dose of 150 mAs.

Figure 1:
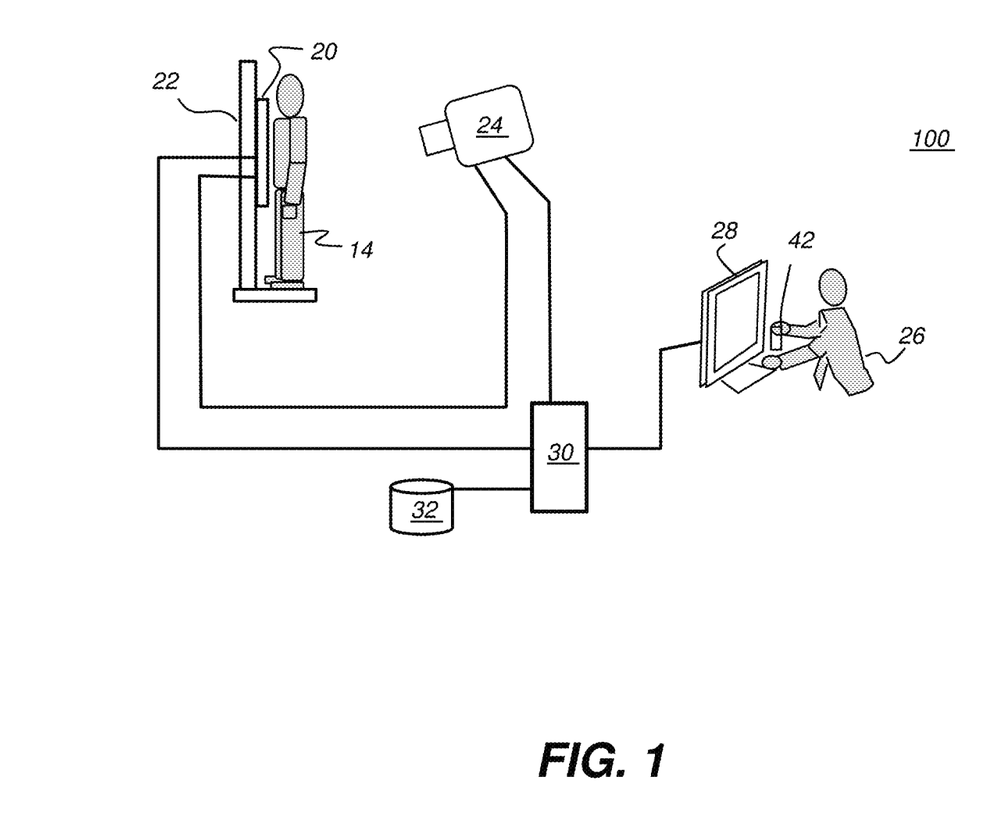
FIG. 1 is a schematic block diagram that shows a radiography apparatus that uses a DR detector with configurable AEC regions.

The schematic block diagram of FIG. 1 shows a radiography apparatus 100 that uses a DR detector 20 with a configurable exposure control measurement feature that uses a preliminary rapid probe exposure to eliminate the need for AEC sensors. A patient 14 is positioned against DR detector 20, such as mounted on a bucky or other support 22, and exposed to a low-level "probe" radiation from an x-ray source 24 for image acquisition. The exposure control measurement regions on DR detector 20 are mapped immediately, in conformance with the size and build of the patient 14 and other factors, following x-ray initiation by the technologist or other practitioner 26. The exposure sequence is initiated using an operator control 42 that is in signal communication with a control logic processor 30 with processing described subsequently. Using this arrangement, no separate AEC sensing devices are separately mounted and configured. The DR detector 20 itself, as a result of the rapid probe exposure and analysis, provides exposure control measurement regions, effectively supplanting the need for an AEC signal that terminates exposure energy when needed. Practitioner 26 controls setup and operation from a workstation 28 having a display or other control console protected from radiation. Control logic processor 30 is in signal communication with other components of apparatus 100 and provides the needed control signals for data acquisition. A memory 32 or other storage apparatus, in signal communication with control logic processor 30, can store the acquired image data.

In order to better understand aspects of the present disclosure, it is useful to consider how the AEC device is conventionally used and to observe some of the shortcomings of conventional AEC deployment that are addressed by the present solution.

Figure 2A:
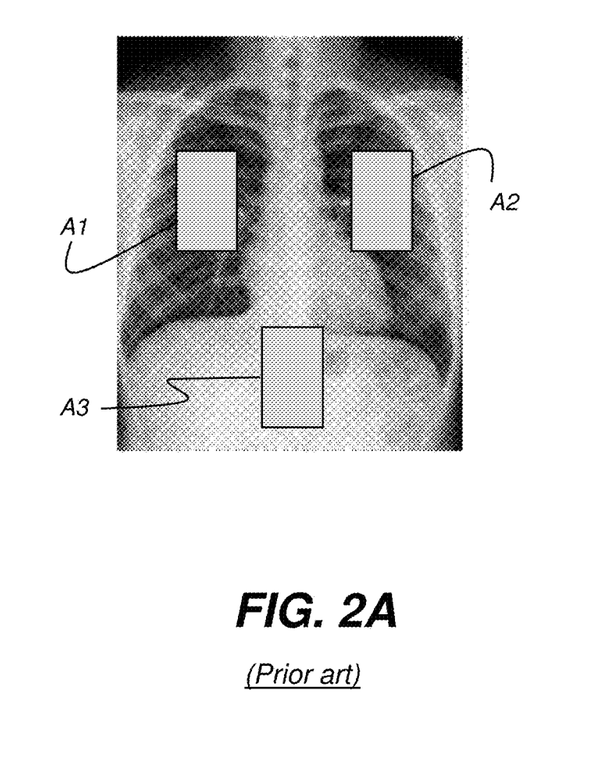
FIGS. 2A and 2B are schematic diagrams that show typical location assignments for automatic exposure control (AEC) sensors.
Figure 2B:
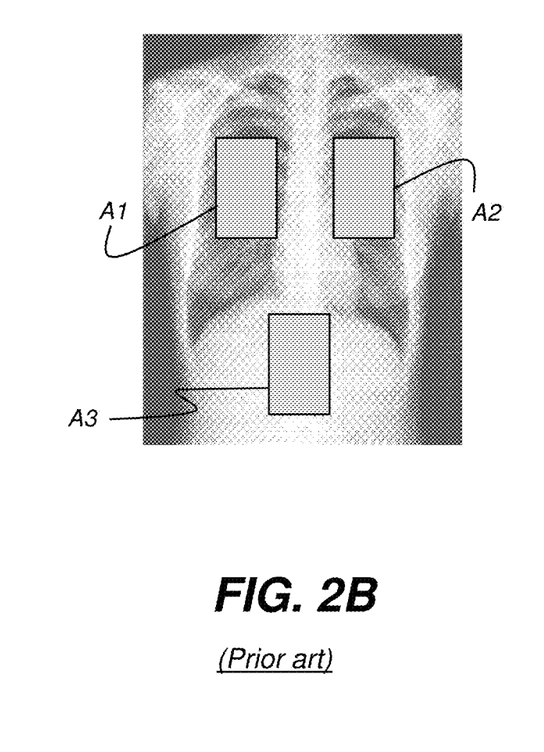

By way of example, FIGS. 2A and 2B show typical AEC location assignments A1, A2, A3 that are conventionally used for different patient sizes and conditions. The given arrangements follow a general pattern that had been established using separate AEC sensing units or using a separate AEC panel with the given set of AEC regions.

Figure 3:
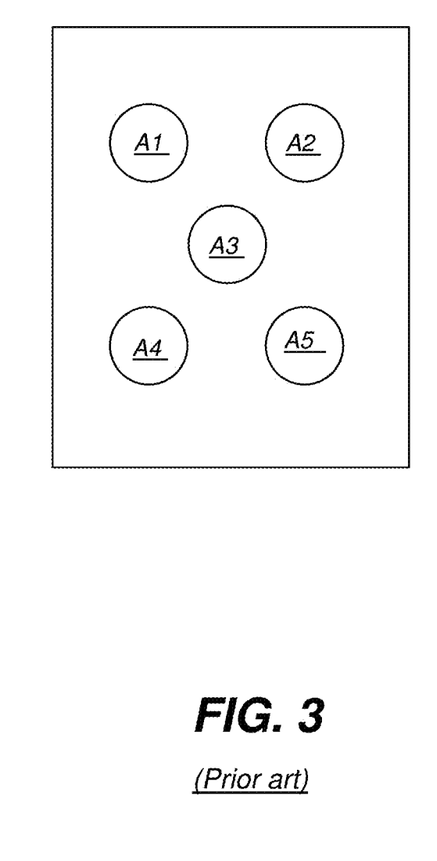
FIG. 3 is a schematic diagram that shows an alternate representative arrangement of dedicated AEC regions at location assignments on a DR detector.

FIG. 3 is a schematic diagram that shows an alternate representative arrangement of dedicated AEC regions at location assignments A1, A2, A3, A4, A5, on a DR detector. In this arrangement, a particular set of the AEC locations can be energized according to operator specification, based on the overall size and stature of the patient.

Figure 4:
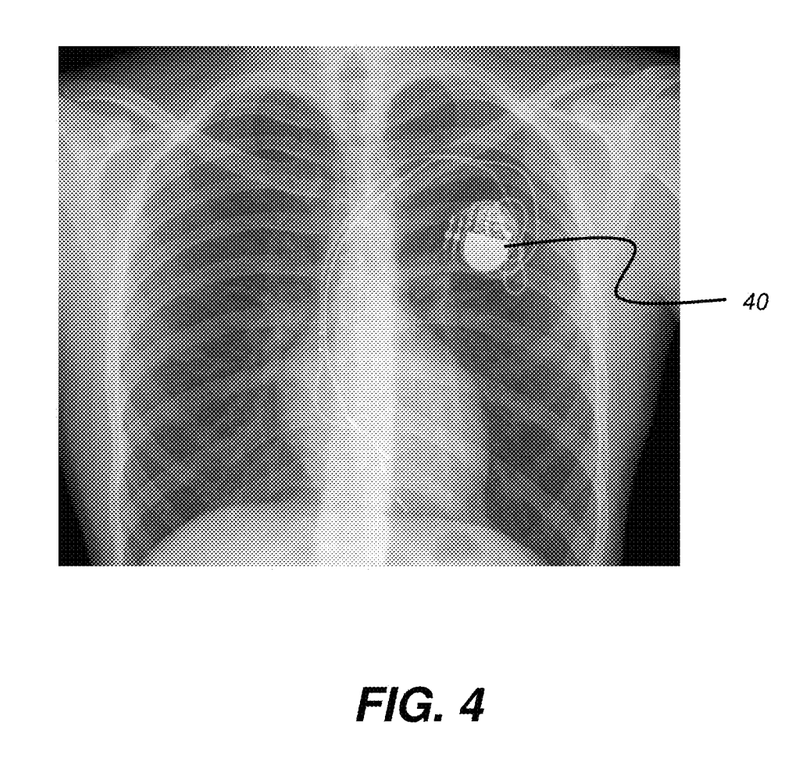
FIG. 4 shows an exemplary chest x-ray for a patient having a pacemaker.

It is useful to note that the AEC positional arrangements typified in FIGS. 2A, 2B and 3 may be useful for a large number of cases, but do not provide for some types of exceptions that are fairly common. FIG. 4 shows one example for which conventional AEC placement does not work well. The patient in this case has a pacemaker 40 in a position along the imaging path that would clearly obstruct the radiation signal to the corresponding lung. The relative position of pacemaker 40 can vary, depending on patient build and stature, making it difficult to reposition the AEC for the lung with sufficient confidence. It can be difficult for the technologist to determine, with precision, the exact location of pacemaker 40 in an individual instance. Still other exceptional cases can involve patients for which a lung or other organ has been removed or other cases wherein anatomy is non-symmetric for some reason.

Figure 5A:
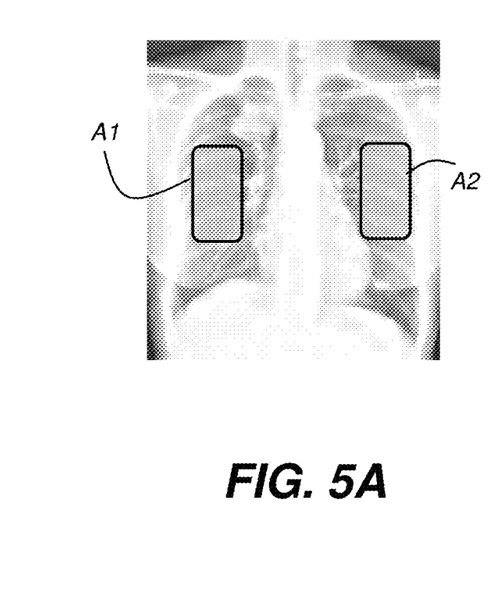
FIGS. 5A and 5B are diagrams that show, respectively, AEC locations for a chest image without a pacemaker, and a chest image with a pacemaker.
Figure 5B:
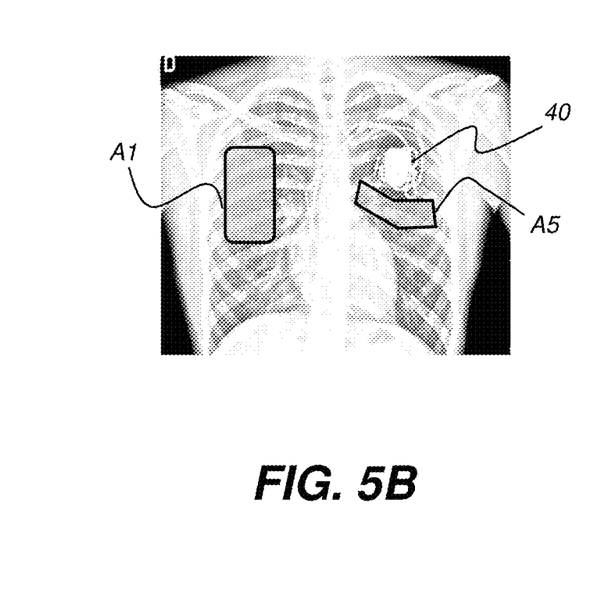

FIG. 5A shows AEC locations A1 and A2 for the normal case, here a chest image with both left and right lungs and no pacemaker. FIG. 5B shows a chest image in which one lung has pacemaker 40. In FIG. 5B, an appropriate AEC location assignment A5 would have a non-conventional shape, skirting edges of pacemaker 40 and along the edge of the lung feature. Alternately, in the FIG. 5B example, AEC placement A5 could be omitted and the AEC data would then be obtained over the AEC location A1. AEC location A1 could alternately be mapped to a nonsymmetric shape in conformance with the corresponding subject anatomy.

It should be noted that it would be difficult for the un-aided practitioner to specify an irregular or geometrically nonsymmetric AEC arrangement as shown in FIG. 5B without accurate knowledge of the underlying anatomy and implanted devices. An embodiment of the present disclosure addresses this difficulty by obtaining an initial, low-exposure probe image that can be analyzed and used to design a suitable configuration for exposure control measurement, including an exposure control region having an irregular, nonsymmetric shape.

Figure 6:
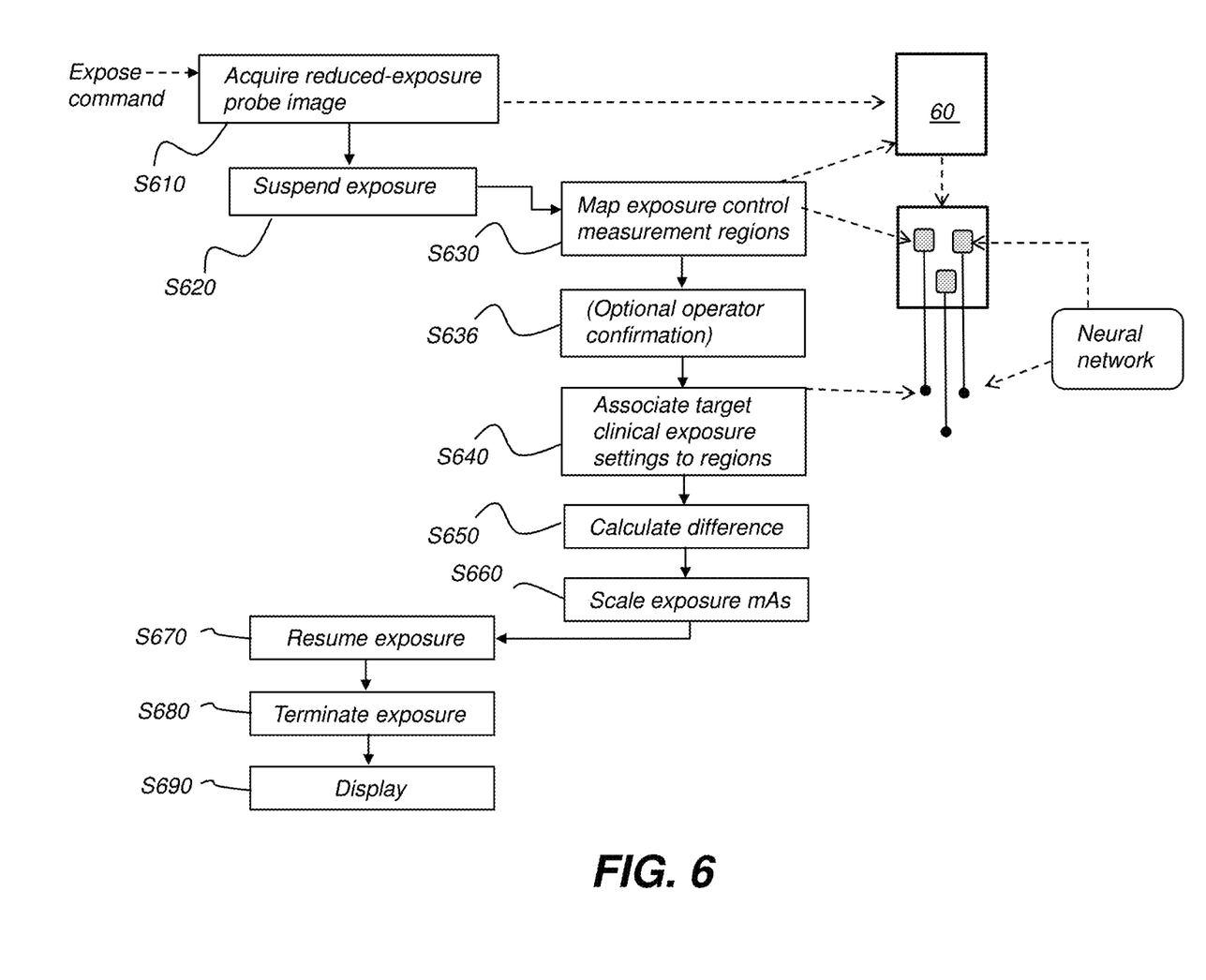
FIG. 6 is a logic flow diagram that shows a sequence for acquiring a digital radiographic image on a DR panel that applies exposure control according to an embodiment of the present disclosure.

Referring to the logic flow diagram of FIG. 6, there is shown a sequence for acquiring a digital radiographic image on a DR panel using an approach that applies exposure control according to an embodiment of the present disclosure. The operator initiates the exposure sequence by entering an expose command, such as by pressing an expose pushbutton that controls an x-ray generator or by entering an instruction on an operator interface console or display. A rapid probe image acquisition step S610 is initiated, in which the radiographic imaging system, with exposure settings set to provide reduced level exposure, acquires a probe image 60, that is, a reduced-exposure image of a subject anatomy on the digital radiography detector panel. The exposure level that is used for the rapid probe image is calculated to be less than about half of the exposure that would be required for clinical imaging. Thus, the probe image 60 that is acquired would not have acceptable quality for diagnostic purposes. Instead, compared against clinically useful images, the reduced-exposure rapid probe image is a relatively noisy image.

The Applicant's method analyzes the reduced-exposure probe image in order to provide exposure control. Subsequent steps executed for clinical image acquisition and following reduced-exposure image acquisition are intended to operate within a very short time interval, imperceptible to the patient. By using high-speed logic, such as a machine-learning algorithm, generated as described subsequently, image evaluation and decision-making processes can be performed within fractions of a second, obviating potential problems of patient movement, for example. In a suspension step S620, x-ray beam generation is temporarily suspended by the system in order to allow processing and system response to the results provided by the reduced-exposure probe image.

A mapping step S630 identifies or maps one or more exposure control measurement regions having boundaries that lie within the reduced-exposure image. With reference to FIGS. 5A and 5B, for example, exposure control measurement regions can correspond to the AEC location assignments A1, A2, and A5 that would conventionally be used. This mapping identifies regions of the image that are readily measured to characterize the effects of the reduced exposure settings generated for step S610. An association step S640 then determines a corresponding predetermined target clinical exposure setting with each of the mapped exposure control measurement regions. The target exposure settings can be stored as metadata that is linked to image content. Alternately, target exposure settings can be computed for one or more bounded regions, using averaged image density or noise characteristics. According to an embodiment of the present disclosure, described in more detail subsequently, target exposure settings can be obtained from a trained machine-learning module.

As the FIG. 6 sequence shows, a machine-learning algorithm can provide the high-speed image recognition that is needed to perform mapping step S630 and association step S640 within a very short time. Training of the machine-learning algorithm for generating a neural network is described in more detail subsequently.

The target clinical exposure setting that is identified in association step S640 is based on factors of noise, resolution, and contrast that are considered acceptable for the corresponding exposure control measurement region. It should be noted that the target clinical exposure setting can be nominally at least about twice the exposure value of the reduced-exposure probe image. The target clinical exposure setting can be a stored value, determined according to technologist practices, or can be calculated from pixel values obtained from images in the training database used by the machine-learning algorithm.

A calculation step S650 calculates a difference for pixel data within the one or more mapped exposure control measurement regions, between the corresponding acquired reduced-exposure acquisition setting used for the rapid probe image acquired in step S610, and mapped in step S630, and the associated target clinical exposure setting obtained in step S640. This calculation can be a ratio or may use the proportional relationship between probe and target image quality or noise characteristics, for example. Based on this calculation, a scaling step S660 then scales the exposure value, such as by adjusting the tube current mAs value or exposure duration time, for capturing a radiographic image having suitable diagnostic quality. A resume exposure step S670 then resumes x-ray beam generation at the system calculated scaled-exposure mAs or timing duration value and directs the generated x-ray beam toward the DR detector in order to acquire and record a clinically acceptable radiographic image. Exposure is terminated automatically in an exposure termination step S680 based on the exposure time determined in the calculation and scaling steps S650, S660. An image display step S690 then obtains and renders the captured, clinical or diagnostic quality x-ray image to the system display.

Probe image evaluation and response carried out in steps S630, S640, S650, and S660 must be executed within a brief period of time, preferably within a time interval that is short enough to be imperceptible to a human subject and short enough so that movement of the subject patient during the momentary delay is unlikely. For example, the total time needed for step S630-S660 execution can be less than one half second, such as an interval of 200 msec or less. In order to provide this execution speed, an embodiment of the present disclosure can employ an algorithm developed using machine learning for rapidly characterizing patient anatomy and configuring the AEC function of the DR panel.

Although a machine-learning algorithm is shown in the sequence of FIG. 6, other logic processing types can alternately be used, including pattern recognition software, for example. Machine learning has advantages of rapid recognition and decision-making that emulates pattern recognition and response capabilities of a human observer. Subsequent description provides more detailed information on how the machine-learning algorithm is trained for high speed anatomy characterization and AEC exposure region mapping.

Optional Operator Confirmation

Following step S630, it can be useful to display the mapped exposure control measurement regions for operator confirmation. To provide this behavior, the operator can specify an image quality assurance (QA) mode of operation that briefly interrupts the sequence of FIG. 6 to obtain operator confirmation in an optional confirmation step S636. According to an embodiment of the present disclosure, a first operator entry, such as a first exposure button press, performs steps S610, S620, and S630, pausing to display the exposure control measurement regions to the operator. These regions can be highlighted on a displayed version of the reduced-exposure image, such as by displaying a color outline of a mapped region for example. A second button press, or other operator entry, confirms operator approval of the mapped region in step S636 and continues operation, resuming exposure as shown in steps S640, S650, S660, and S670. Alternately, if the operator rejects the mapped region, the operator is prompted to adjust region boundaries before continuing or in order to cancel subsequent exposure. The machine learning algorithm can use these operator approval/disapproval steps for training.

Machine Learning for the Probe Image Evaluation Algorithm

Conventional image processing techniques for defining boundaries of AEC sensing regions on the DR panel would apply approaches using pattern recognition and segmentation algorithms that partition image content into discrete, recognizable components. These conventional approaches can be highly computation-intensive and often require considerable computing resources and processing time. It would be feasible to adapt conventional solutions to the problem of rapid evaluation and adjustment of exposure control regions for each individual imaged subject, such as for patients receiving service at a radiographic imaging facility. However, the noted shortcomings of conventional image processing approaches tend to discourage their application to probe image evaluation.

As noted with respect to FIG. 6 in the preceding discussion, a machine-learning algorithm that evaluates the reduced-exposure probe image using neural network logic can operate efficiently if appropriately trained. However, there are a number of considerations and constraints for providing and managing the training process for radiography applications. For example, in practice, it is most desirable to avoid unnecessary exposure wherever possible. It is highly preferable that training methods for probe image evaluation avoid requiring additional exposure to radiation for generating a base set of patient images.

A database of previously acquired x-ray images can be used for the training and evaluation function, but this presents some level of difficulty. Since reduced-exposure images are not clinically usable, typically because of their high noise content, such images are not generally archived and may even be discarded; instead, images that are saved and stored in a database of medical images are most often images having clinical or diagnostic quality. Obtaining a sufficient database of reduced-exposure probe images suitable for training and generating neural network logic is not desirable, since this works against the goal of avoiding unnecessary patient exposure.

Faced with the need to use existing clinical quality images in order to provide a benchmark database for evaluation of low-exposure probe images for machine learning response, the Applicants have employed a simulation approach. According to an embodiment, the Applicants' approach for generating the training database is to use and modify a set of exemplary stored images, obtaining different types of data from the set of stored images, and optionally conditioning each of the stored images in the set in order to simulate the noise and other features that would be evident in reduced-exposure probe images of the same subject. This set of conditioned images is then used in two ways: as a resource for obtaining target exposure values and as a training database for the machine-learning algorithm that characterizes the subject anatomy and that maps suitable regions of the DR detector panel for exposure control in subsequent image acquisition. The same kVp settings can be used for images from the training database and reduced-exposure probe images.

In addition to image data analysis, the sequence shown with respect to FIG. 6 also takes advantage of metadata that can be provided with the archived image content, including information on exposure settings used to acquire each image. Knowing the exposure settings used for images in the training set can be helpful, for example, with respect to association step S640 in the FIG. 6 sequence.

According to an embodiment of the present disclosure, a database of previously acquired images is employed both as a training database for image recognition and exposure detection logic and as a basis for calculating target exposure values that relate to each of a number of types of radiographic image. The previously acquired images are generated at clinical exposures; image quality can be modified as described herein in order to simulate image content acquired at reduced exposures. Thus, the machine-learning training function is not a straightforward "deep learning" function but includes calculation of exposure metrics used in subsequent processing of images and can also require supplemental transformation of the data derived from the training database.

Figure 7:
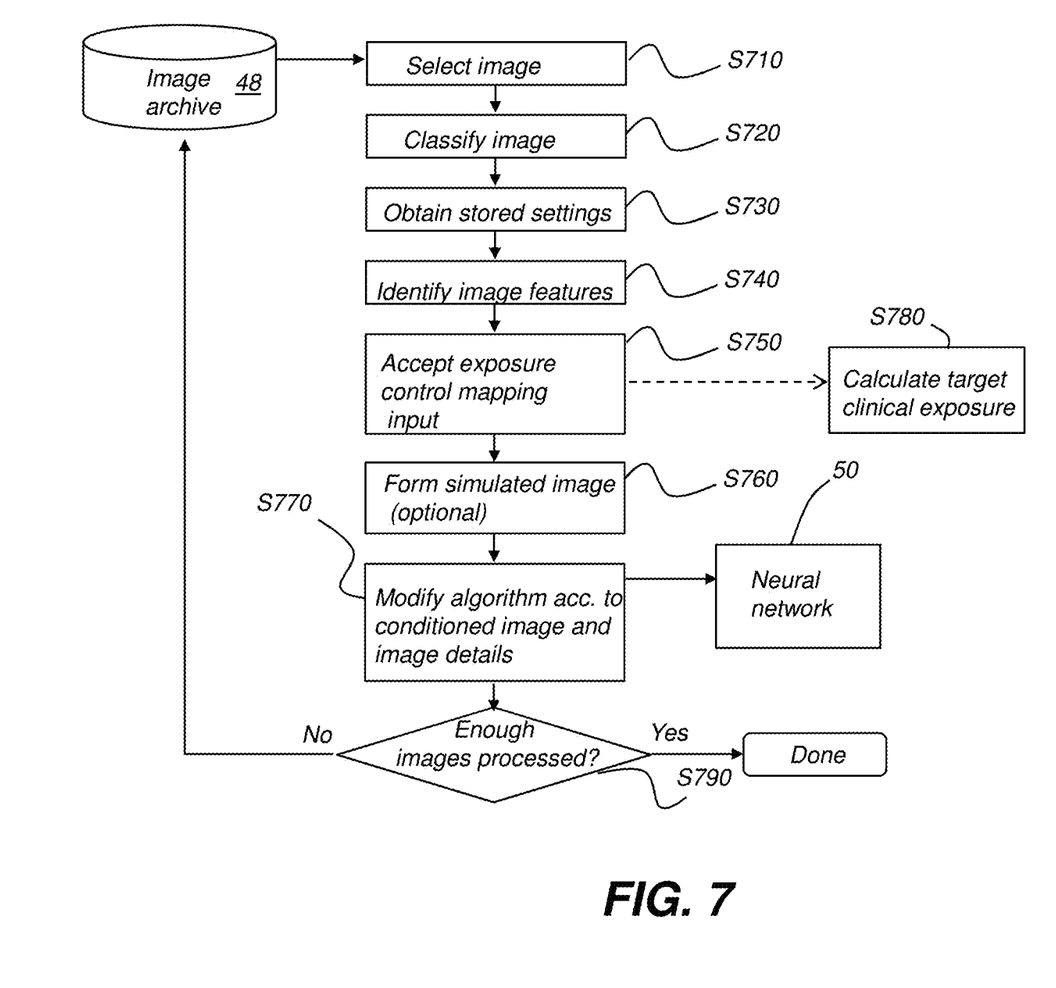
FIG. 7 is a logic flow diagram that shows a sequence for generating a machine learning algorithm according to an embodiment of the present disclosure.

The logic flow diagram of FIG. 7 shows a sequence for processing a set of radiographic images in order to form the neural network logic and calculate the target exposure levels described in steps S630 and S640 of FIG. 6. The iterative sequence of FIG. 7 operates successively upon each image from an image archive 48, improving a machine-learning algorithm for processing radiographic image content with each iteration.

In the sequence of FIG. 7, steps S710, S720, S730, and S740 can be useful for classifying the image content for each individual image of particular subject anatomy from the training database.

In an image selection step S710, an image is obtained from an electronic image archive 48 that stores a set of radiographic images of suitable anatomy for training. Images in image archive 48 are selected as representative of the types of images that are captured, processed, and stored by the radiographic imaging system and having sufficient image quality.

In an image classification step S720, the selected image can be classified as to type of image (e.g. chest image, AP or PA view, extremity, bone, etc.) according to the subject anatomy imaged. An optional settings acquisition step S730 obtains any useful information on stored settings that relate to the subject anatomy imaged; stored settings can include metadata corresponding to the acquired image and can also include information on technique settings used for image capture for example. In an optional image feature identification step S740, features used for relating the imaged subject anatomy to other similar anatomy can be identified. For example, the overall outline of the upper torso can be a useful image feature for identification and classification by the algorithm. Features identification step S740 can also identify special cases and imaging anomalies, such as clipping, poorly placed DR receiver, anatomy obscured by pacemaker or other device, missing organs, and other characteristics of an image.

At the conclusion of step S740, relevant image data content for the training image is identified; subsequent processing can apply this information in order to recognize the image type and more accurately define regions of the image that are most useful for exposure measurement and control.

A mapping acceptance step S750 then executes, displaying features of the acquired image and accepting input from a trained observer. With relation to the present embodiment, trained observer input is used for designating exposure control regions at this point in the FIG. 7 training sequence. For step S750, the trained observer can be positioned at a display console or monitor, which displays a rendering of the image that was selected in step S710. The observer, manually or with the aid of segmentation software, traces or otherwise defines the outline or boundaries of one or more areas of the DR detector panel designated for exposure control. The tracing can be entered using a mouse or other stylus, for example. Alternately, the trained observer can use a touch screen entry in order to specify the bounded region of the image that serves as an indicator of exposure received.

In the FIG. 7 sequence, acceptance of the mapping in step S750 also updates a target calculation step S780 that calculates an exposure metric for the mapped exposure control region. The target clinical exposure setting can be computed from the training set and include values from images of the subject anatomy from different patients. The target values can be configured based on a number of factors, such as anatomy region, dimensions, and view positions. This calculated, predetermined metric is indicative of the exposure level used for obtaining a clinical image and can be an averaging of pixel values within the defined exposure control region or can use some other method for generating and updating a target exposure value with each archived image that is processed as part of the training set. Calculation in step S640 (FIG. 6) uses this metric from step S780 in order to determine scaling factors for exposure mAs in steps S650, S660.

With boundaries of the exposure control measurement region defined in step S750, the information needed for training the algorithm to automatically assign pixel membership to exposure control measurement regions, based on probability from a large number of test cases, is complete. However, as described with reference to FIG. 6, the algorithm that is actually applied for exposure control measurement region setup must operate with under-exposed images. Thus, according to an alternative embodiment, the method shown in FIG. 7 can execute an image conditioning step S760 in which the full-exposure image acquired in step S710 is modified in order to simulate the reduced-exposure probe image that will be acquired in practice in step S610 of the FIG. 6 sequence. For this purpose, image processing can add a suitable amount of noise to each image before proceeding to step S770. A measure of noise compensation can be used to adapt training results for the images that will be analyzed in practice.

A trained algorithm modification step S770 then incorporates the new image mapping data from steps S750 and S760 and modifies the existing neural network logic 50 accordingly. To execute iterative looping, a test step S790 is shown, continuing to process additional images from image archive 48 as needed until sufficient images have been considered.

Training can be performed at imaging system fabrication or in the field. It should further be noted that the generation of neural network logic can be ongoing, continuing the training of the image recognition and exposure region mapping functions in day-to-day practice as needed to refine system response. The steps shown in FIG. 7 would be modified accordingly, bypassing one or more steps of the sequence as needed, depending on characteristics of the image content and the need to update and improve neural network logic 50 and target exposure data.

Techniques and utilities for neural network logic generation are well known to those skilled in the machine-learning arts. Logic for defining the exposure control regions proceeds, analyzing a database of training images in an iterative process. Within each image, pixels or groupings of pixels are assigned weightings that relate to the relative probability that these pixels or groupings are included within the defined exposure control region. As additional images are processed in subsequent iterations, a relative weighting can be adjusted with each iteration to more accurately characterize the probability distribution that applies with each pixel for an image type. After a number of images have been processed, the relative pixel weightings tend to stabilize, changing very little and providing neural network response that identifies an exposure control region with close approximation to region identification achieved by a trained observer. According to an embodiment of the present disclosure, training can be considered complete when system response is not perceptibly changed, with little or no change to the neural network logic 50 after a given number of iterations.

According to an aspect of the present disclosure, one or more radiography workstation components may participate in implementing the training phase. The methods by which training can be done include, but are not limited to, Support Vector Machines, Neural Networks, Decision Trees, naive Bayes, Logistic Regression, and other techniques from supervised, semi-supervised, and unsupervised learning. A training or "model-derivation" aspect of the method may be practiced with any available training techniques that yield a method for classification. Once the training is complete, a number of models can be derived and used for different image types.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for capturing a diagnostic quality digital radiographic (DR) image of a subject, the method comprising:
    capturing a reduced exposure DR image of a particular anatomical region of the subject in a DR detector using an x-ray source set at a reduced exposure level;
    mapping one or more exposure control regions in the reduced exposure DR image based on one or more previously captured diagnostic quality DR images of the same particular anatomical region of other subjects;
    calculating a difference between an exposure level used for the mapped regions in the previously captured diagnostic quality DR images and the reduced exposure level;
    setting the x-ray source at a diagnostic exposure level according to the calculated difference; and
    capturing the diagnostic quality DR image of the particular anatomical region of the subject in the DR detector using the x-ray source set at the diagnostic exposure level, wherein the step of setting the x-ray source includes setting an energy level of the x-ray source and a time duration of exposure by the x-ray source.

2. The method of claim 1, wherein the step of setting the x-ray source includes determining an imaging region of the subject, a size of the subject, and anatomy view angles of the subject.

3. The method of claim 1, wherein the step of mapping comprises receiving an output by a trained machine learning algorithm using a plurality of stored DR images.

4. The method of claim 3, further comprising capturing the stored DR images at clinical exposure levels set at more than the reduced exposure level.

5. The method of claim 3, further comprising training the trained machine learning algorithm using archived DR images captured at the reduced or standard diagnostic exposure levels and corresponding copies of the archived DR images having image noise induced therein to mimic exposure levels lower than standard diagnostic exposure levels.

6. The method of claim 1, further comprising displaying the reduced exposure DR image of the subject having the one or more exposure control regions highlighted.

7. The method of claim 1, further comprising setting the diagnostic exposure level at a higher mAs than the reduced exposure level and at a same kVp setting as the reduced exposure level.

8. The method of claim 1, further comprising mapping boundaries of the exposure control regions to exclude non-anatomy devices in the subject.

9. A computer implemented method for capturing a diagnostic quality digital radiographic (DR) image of a subject, the method comprising:
   in response to an operator command entry, capturing a reduced exposure DR image of a particular anatomy of the subject in a DR detector using an x-ray source set at a reduced exposure level;
   mapping one or more exposure control regions in the reduced exposure DR image using an output from a machine learning algorithm trained on a plurality of archived diagnostic quality DR images of the same particular anatomy of other subjects;
   calculating a difference between an exposure level used for the mapped regions in the plurality of archived DR images and the reduced exposure level;
   automatically setting the x-ray source at a diagnostic exposure level at least about twice higher than the reduced exposure level; and
   capturing the diagnostic quality DR image of the particular anatomy of the subject in the DR detector using the x-ray source set at the diagnostic exposure level.

10. The method of claim 9, further comprising training the machine learning algorithm using the plurality of archived DR images having exposure control regions marked thereon by a human operator.

11. The method of claim 9, further comprising training the machine learning algorithm using an iterative sequence comprising:
   selecting an image from a database of the archived DR images; and
   identifying at least one exposure control region in the selected image using input from a trained human observer.

12. The method of claim 9, further comprising executing the steps of the method automatically in response to a single operator command entry.

13. The method of claim 12, further comprising entering the single operator command entry using a pushbutton.

14. The method of claim 1, further comprising setting the diagnostic exposure level at least about twice the reduced exposure level.

15. The method of claim 12, further comprising executing the steps of the method automatically in less than about one-half second in response to the single operator command entry.

16. A computer implemented method for capturing a digital radiographic (DR) image of a subject, the method comprising:
   in response to an operator command entry, capturing a reduced exposure DR image of the subject in a DR detector, including exposing the subject using an x-ray source set at a reduced exposure level;
   mapping one or more exposure control regions in the reduced exposure DR image and associating a predetermined exposure level with the one or more exposure control regions, using an output from a machine learning algorithm;
   calculating a difference between the predetermined exposure level setting and the reduced exposure level;
   automatically setting the x-ray source at a diagnostic exposure level according to the calculated difference;
   capturing a diagnostic DR image of the subject in the DR detector, including exposing the subject using the x-ray source set at the diagnostic exposure level; and
   setting an exposure time of the x-ray source according to the calculated difference.

17. The method of claim 9, further comprising displaying the one or more exposure control regions for confirmation by an operator before the step of calculating.

18. The method of claim 17, further comprising performing both the steps of capturing the reduced exposure DR image and mapping one or more exposure control regions in response to a first pushbutton press by the operator, and performing the steps of calculating, automatically setting, and capturing the diagnostic quality DR image in response to a second pushbutton press by the operator.

19. The method of claim 9, further comprising mapping one or more exposure control regions in the reduced exposure DR image to exclude man-made devices therefrom.

* * * * *